United States Patent [19]
Chen et al.

[11] Patent Number: 6,119,850
[45] Date of Patent: Sep. 19, 2000

[54] AIR FRESHENER CONTAINER

[76] Inventors: Kai-Hung Chen, 21 Fl.-3, No.302, Chi-Hsien-I Rd., Hsin-Hsing Dist.; Hsun-Shen Han, 2 Fl.-2., No. 3, Lane. 42, Tung-Men Rd., Ku-Shan Dist., both of Kaohsiung, Taiwan

[21] Appl. No.: 09/358,276

[22] Filed: Jul. 21, 1999

[51] Int. Cl.[7] .................................................. B65D 83/00
[52] U.S. Cl. ............................................. 206/0.5; 206/457
[58] Field of Search ................................ 206/457, 459.1, 206/459.5, 0.5, 823, 581; 273/DIG. 24

[56] References Cited

U.S. PATENT DOCUMENTS 3,734,509  5/1973  Glass et al. ...................... 273/DIG. 24
4,593,817  6/1986  Ferrero ..................................... 206/457
5,551,569  9/1996  Garvin-Mazzarisi .................... 206/457

*Primary Examiner*—Jacob K. Ackun
*Attorney, Agent, or Firm*—Woodcock Washburn Kurtz Mackiewicz & Norris LLP

[57] ABSTRACT

An air freshener container includes a first casing and a second casing attached to each other so as to form an animal model body, moreover the head and the hat are pivotally mounted in the animal model body. The tie, transparent cover and foot are attached to the first casing of the animal model body, and the signal sensor is attached to the second casing. The lighting unit extending to the transparent cover is attached to the signal sensor, and the container of air freshener is detachably received in the through hole of the animal model body.

10 Claims, 5 Drawing Sheets

AIR FRESHENER CONTAINER

CROSS-REFERENCES TO RELATED APPLICATIONS

Not Applicable.

BACKGROUND OF THE INVENTION

1. Field of the Invention

The present invention relates to an air freshener container having an animal model body.

2. Description of the Related Art

A conventional air freshener container is not a simple container with a decorative pattern. The appearance of contemporary designs vary greatly and include such shapes such as an animal, a plant, a cartoon character or many other objects. Previous construction of air freshener containers did not allow the external configuration to be changed.

Furthermore the container loses its novelty over time, because the external figure cannot be unchanged. Since the air freshener container's only purpose is to serve as a simple decorative container with virtually no other use, its useful scope is not broad.

The present invention has arisen to mitigate and obviate the disadvantage of the conventional air freshener container.

BRIEF SUMMARY OF THE INVENTION

In accordance with one aspect of the present invention, an air freshener container is provided that has a changeable pose, can be assembled by the user and doubles as a visual prompter.

The main body of the air freshener container is a simple assembly which has a hollow body with an animal shape. The animal-shaped body includes a first casing and a second casing abutting each other. The air freshener container has a head pivotally mounted in the top of the main body and users can change the pose of the air freshener container by turning the head. So consumer can enjoy the fun of assembling their own design.

The container has a transparent cover attached to the anterior casing and has a lighting unit attached to a signal sensor. The lighting unit will blink when a mobile phone receives a call so as to provide a prompt function.

Further benefits and advantages of the present invention will become apparent after a careful reading of the detailed description with appropriate reference to the accompanying drawings.

DETAILED DESCRIPTION OF THE INVENTION

Figure 1:
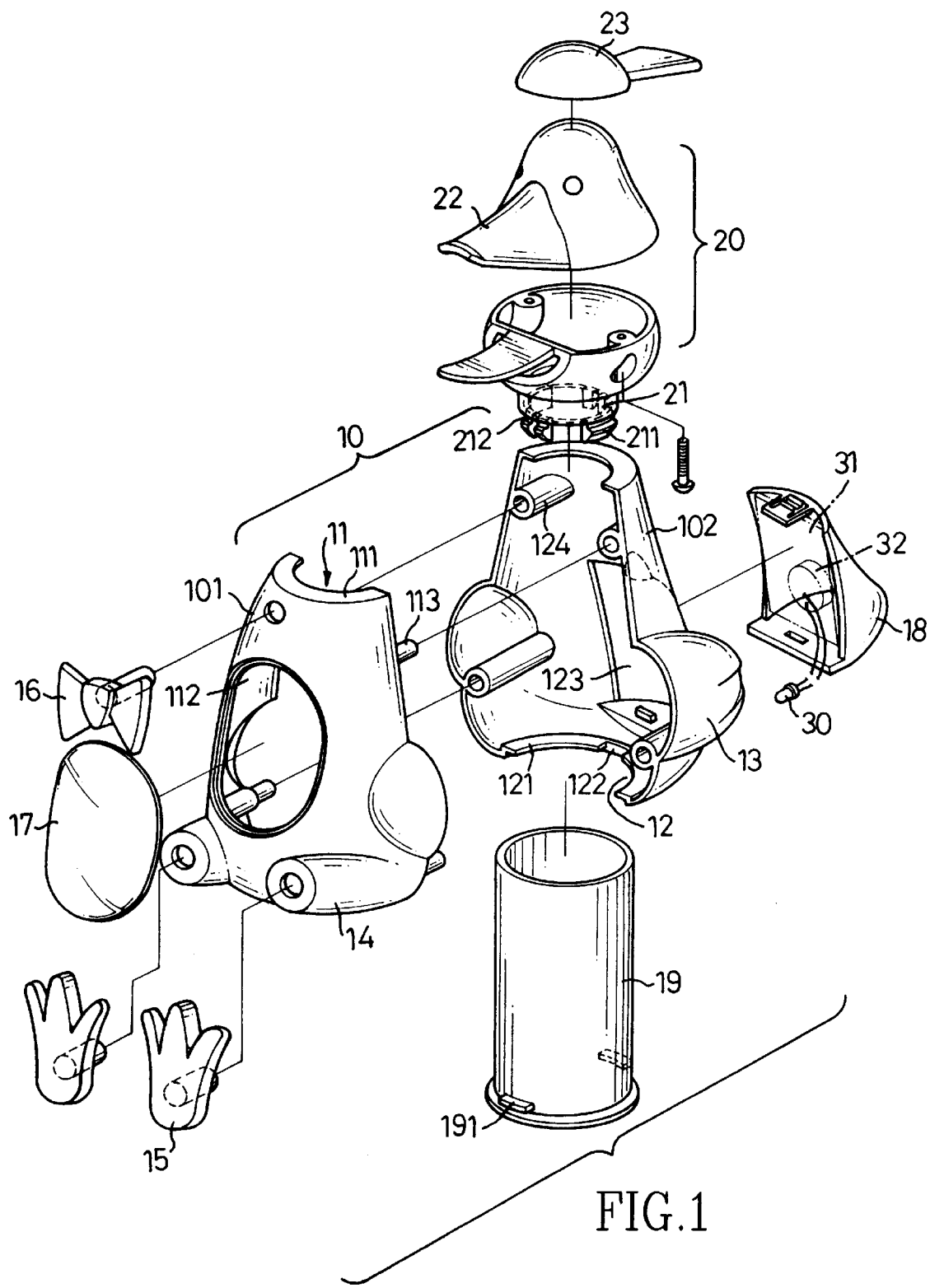
FIG. 1 is an exploded perspective view of an air freshener container in accordance with the present invention.
Figure 2:
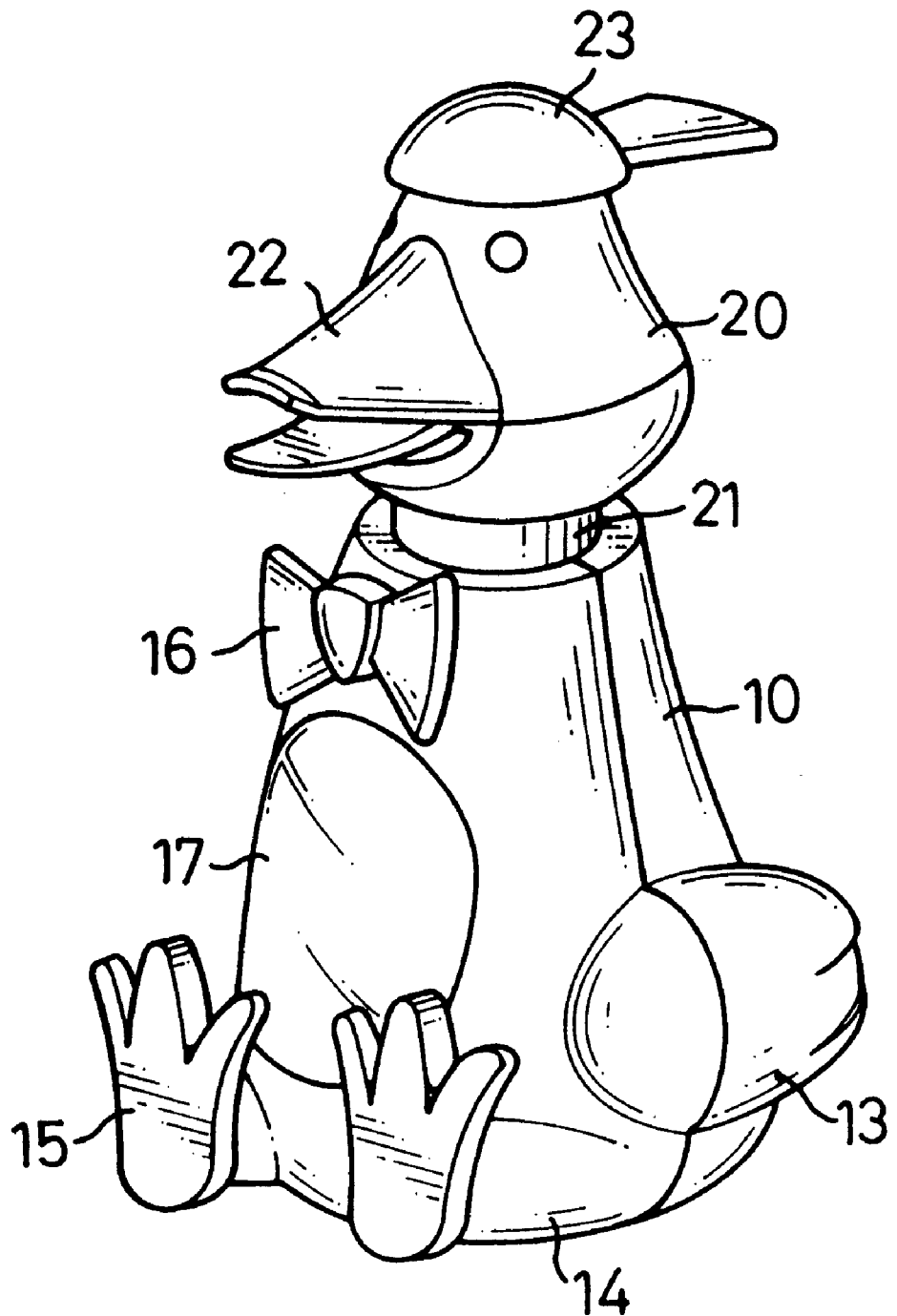
FIG. 2 is perspective view of the air freshener container in FIG. 1.
Figure 3:
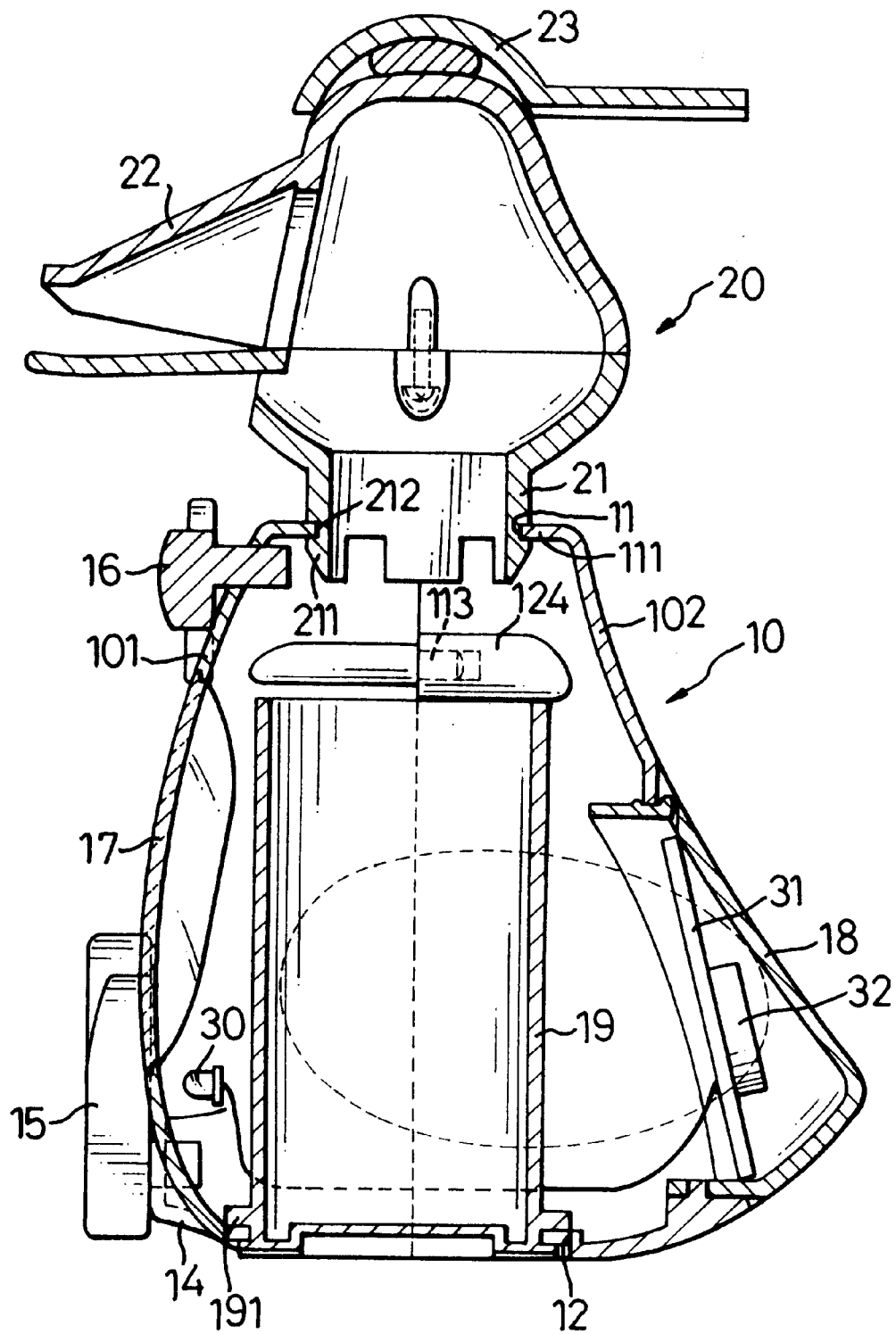
FIG. 3 is a side plan cross-sectional view of the air freshener container in FIG. 1.

Referring to the drawings and initially to FIGS. 1–3, an air freshener container in accordance with the present invention comprises a hollow body (10), a head (20) pivotally mounted in the animal model body (10), a lighting unit (30) abutted the body (10) having a shape such as a duck and a container (19) mounted in the body (10) to hold air freshener.

The body (10) includes a first casing (101) and a second casing (102) abutting each other. The first casing (101) has four stubs (113) and the second casing (102) has four sockets (124) to receive the four stubs (113) of the first casing (101). The top of the body (10) contains a hole (11) that has a flange (111) extending radially inward. The bottom of the body (10) contains a through hole (12) which has an annular flange (121) extending radially inward therefrom, and contains two notches (122) on opposite sides of the flange (121).

Figure 4:
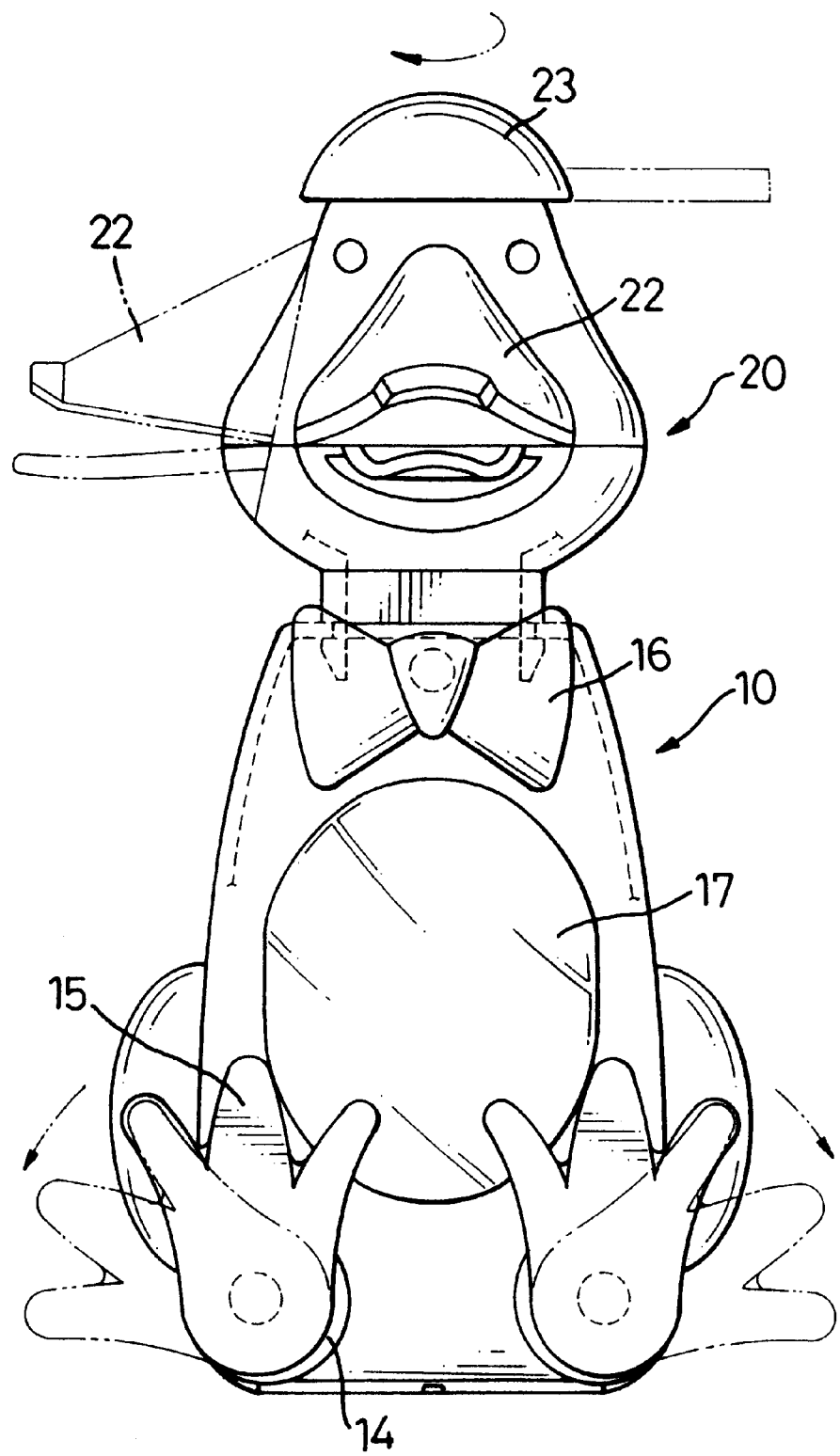
FIG. 4 is a front operational view of the air freshener container in FIG. 1.
Figure 5:
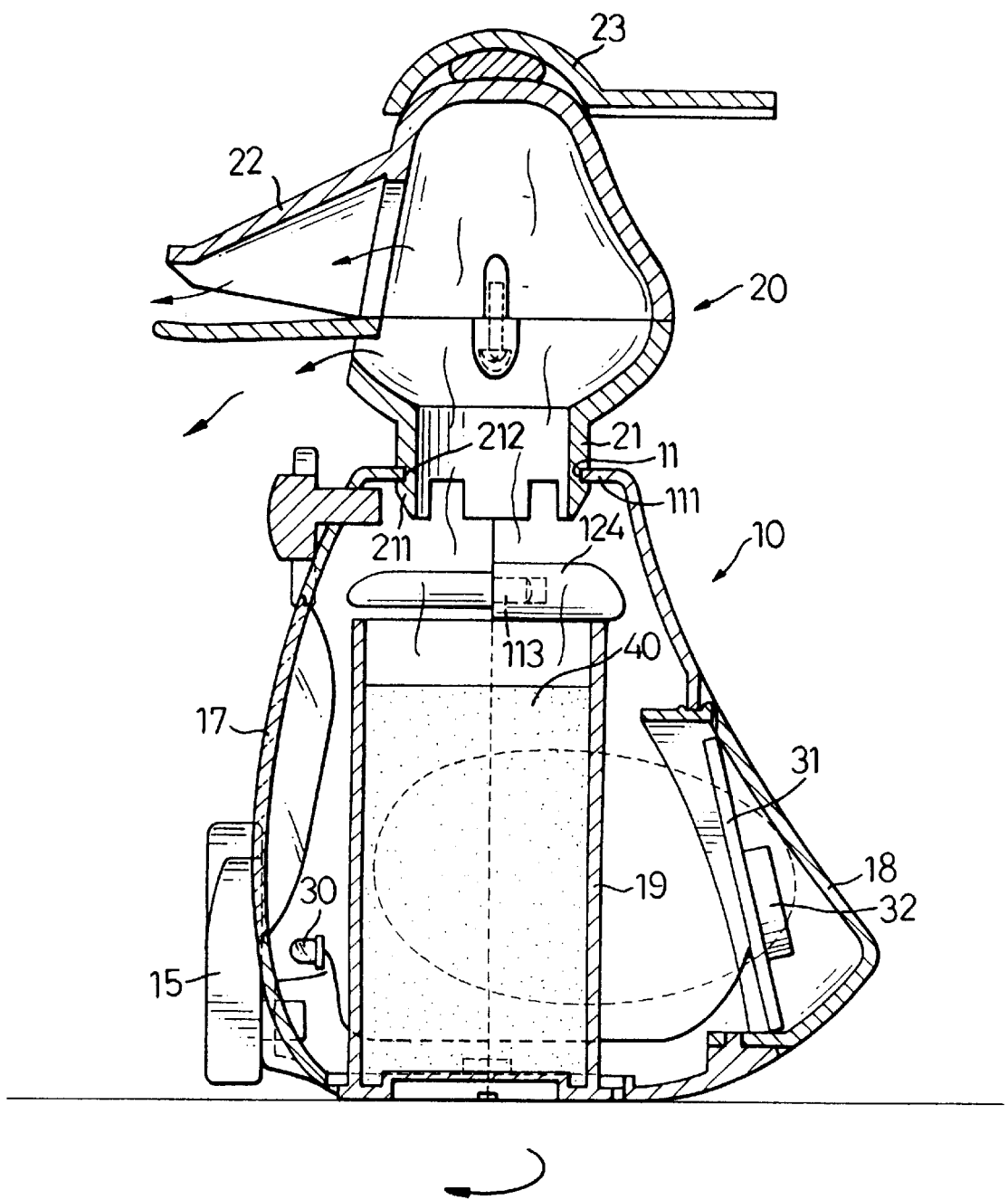
FIG. 5 is a side plan cross-sectional view of the air freshener container in FIG. 1 in use.

The head (20) includes one portion with the neck (21) and another potion with the upper bill (22) abutting each other. The bottom of the neck (21) has multiple snaps (211) extending therefrom and containing a groove (212). The snaps (211) have a diameter greater than the inner diameter of the flange (111) of the hole (11). The flange (111) of the hole (11) is received in the groove (212) of the snaps (211). Thus the head (20) can be turned around to change its pose as shown in FIG. 4. The head (20) further includes a hat (23) attached to the top thereof such as by an adhesive or tape.

The body (10) includes a container (19) having two lugs (191) aligned with the notches (122). The container (19) must be turned when the lugs are through the notches (122) to lock it in place so that the bottom of the container (19) abuts the interior of the annular flange (121) of the through hole (12) so as to be detachably mounted on the bottom of the body (10).

The first casing (101) of the body (10) includes two legs (14) on the bottom thereof. The body (10) includes two feet (15) which pivotally mount on the legs (14) as shown in FIG. 4. The body (10) further includes and a tie (16) attached to the upper portion of the first casing (101). The first casing (101) of the body (10) includes a transparent cover (17) received in an opening (112) thereof.

The second casing (102) of the body (10) contains a square hole (123) and a tail cover (18). The tail cover detachably attaches to the back of the body (10). The second casing (102) of the body (10) forms two wings (13) on the lower portion thereof.

The lighting unit (30) includes a signal sensor (31) attached to the interior of the tail cover (18) and a battery (32) attached to the signal sensor (31). The lighting unit (30) has a first end attached to the signal sensor (31) and a second end extending to the transparent cover (17) of the animal model body (10). The lighting unit (30) blinks when the signal sensor (31) receives a signal such as the radio wave of a mobile phone.

Although the invention has been explained in relation to its preferred embodiment, it is to be understood that many other possible modifications and variations can be made without departing from the spirit and scope of the invention as hereinafter claimed.

What is claimed is:

1. An air freshener container comprising:
   a hollow body (10) including a bottom containing a through hole (12) and a container (19) received in said body (10) and fastened to said through hole (12); and
   a lighting unit (30) attached to said body (10).

2. The air freshener container in accordance with claim 1, wherein said body (10) includes a first casing (101) and a second casing (102) attached to each other.

3. The air freshener container in accordance with claim 1, wherein said body (10) includes a top containing a hole (11), and said air freshener container further comprises a head (20) having a bottom pivotally mounted in said hole (11).

4. The air freshener container in accordance with claim 3, wherein said hole (11) of said body (10) has a flange (111) extending radially inward, and said head (20) has a plurality of snaps extending from said bottom of said head (20) locked in said hole (11).

5. The air freshener container in accordance with claim 1, wherein said through hole (12) of said body (10) includes an annular flange (121) extending radially inward and containing at least two notches (122), and said container (19) has at least two lugs (191) abutting said annular flange (121).

6. The air freshener container in accordance with claim 1, wherein said body (10) includes two wings (13) and two legs (14), and each of said two legs (14) has a foot (15) pivotally mounted thereon.

7. The air freshener container in accordance with claim 2, wherein said first casing (101) contains an opening (112), and said body (10) further comprises a tie (16) attached to said first casing (101) and a transparent cover (17) received in said opening (112) of said first casing (101).

8. The air freshener container in accordance with claim 7, wherein said second casing (102) contains a hole (123), and said body (10) further comprises a tail cover (18) detachably mounted in said hole (123).

9. The air freshener container in accordance with claim 8, wherein said lighting unit (30) includes a signal sensor (31) attached to said tail cover (18) of said body (10).

10. The air freshener container in accordance with claim 9, wherein said lighting unit (30) includes a first end and a second end, said first end attached to said signal sensor (31) and said second end extending to said transparent cover (17).

\* \* \* \* \*

UNITED STATES PATENT AND TRADEMARK OFFICE
CERTIFICATE OF CORRECTION

PATENT NO. : 6,119,850
DATED : January 28, 2001
INVENTOR(S) : Hung Chen et al.

It is certified that error appears in the above-indentified patent and that said Letters Patent is hereby corrected as shown below:

Column 1, line 35, please delete "animal shaped" (as per amendment dated July 21, 1999);
Column 1, line 37, please delete "main" (as per amendment dated July 21, 1999);
Column 2, line 3, the phrase "having a shape such as a duck" should not be here but on
Column 2, line 1, after (10) (as per amendment dated July 21, 1999);

Signed and Sealed this

Twenty-ninth Day of May, 2001

Attest:

NICHOLAS P. GODICI

Attesting Officer     Acting Director of the United States Patent and Trademark Office